(12) United States Patent
Koh et al.

(10) Patent No.: US 9,254,348 B2
(45) Date of Patent: Feb. 9, 2016

(54) IN SITU CROSSLINKING HYDROGEL COMPRISING γ-POLYGLUTAMIC ACID AND METHOD FOR PRODUCING THE SAME

(71) Applicant: SAMYANG BIOPHARMACEUTICALS CORPORATION, Seoul (KR)

(72) Inventors: Young-Joo Koh, Daejeon (KR); Hea-Kyung Kim, Daejeon (KR); Sun-Woo Kim, Daejeon (KR); Guw-Dong Yeo, Daejeon (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 0 days.

(21) Appl. No.: 14/363,022

(22) PCT Filed: Dec. 28, 2012

(86) PCT No.: PCT/KR2012/011774
§ 371 (c)(1),
(2) Date: Jun. 5, 2014

(87) PCT Pub. No.: WO2013/100715
PCT Pub. Date: Jul. 4, 2013

(65) Prior Publication Data
US 2014/0336276 A1    Nov. 13, 2014

(30) Foreign Application Priority Data
Dec. 30, 2011    (KR) .................. 10-2011-0147558

(51) Int. Cl.
*A61L 24/04* (2006.01)
*A61K 47/34* (2006.01)
*C08J 3/075* (2006.01)
*C08G 69/10* (2006.01)
*C08G 69/48* (2006.01)
(Continued)

(52) U.S. Cl.
CPC ............... *A61L 24/046* (2013.01); *A61K 47/34* (2013.01); *A61L 24/0031* (2013.01); *C08G 69/10* (2013.01); *C08G 69/48* (2013.01); *C08G 73/02* (2013.01); *C08J 3/075* (2013.01); *C08J 3/246* (2013.01); *C08J 2371/02* (2013.01); *C08J 2377/02* (2013.01)

(58) Field of Classification Search
None
See application file for complete search history.

(56) References Cited

U.S. PATENT DOCUMENTS 5,162,430 A    11/1992    Rhee
5,385,606 A    1/1995    Kowanko
(Continued)

FOREIGN PATENT DOCUMENTS

EP    1 723 855    11/2006
JP    09-103479    4/1997
(Continued)

OTHER PUBLICATIONS

WO 2007034795 A1, Mar. 2007, Derwent Ab.*
(Continued)

*Primary Examiner* — Satya Sastri
(74) *Attorney, Agent, or Firm* — Lex IP Meister, PLLC

(57) ABSTRACT

Disclosed are a biodegradable, biocompatible hydrogel that can be used for sealants of suppressing the leakage of blood or air during surgical operation, tissue adhesives, anti-adhesive agents and drug delivery carriers, and a method for producing the same.

19 Claims, 4 Drawing Sheets

(51) Int. Cl.
*C08J 3/24* (2006.01)
*A61L 24/00* (2006.01)
*C08G 73/02* (2006.01)

(56) References Cited

U.S. PATENT DOCUMENTS

| | | | |
|---|---|---|---|
| 5,874,500 | A | 2/1999 | Rhee |
| 6,566,406 | B1 | 5/2003 | Pathak |
| 6,602,952 | B1 | 8/2003 | Bentley |
| RE38,827 | E | 10/2005 | Barrows |
| 2005/0028930 | A1 | 2/2005 | Powell |
| 2005/0107543 | A1 | 5/2005 | Angelucci |
| 2006/0078536 | A1 | 4/2006 | Kodokian |
| 2007/0125978 | A1 | 6/2007 | Ho |
| 2010/0144902 | A1 | 6/2010 | Shu |
| 2011/0009327 | A1 | 1/2011 | Hill |

FOREIGN PATENT DOCUMENTS

| | | | |
|---|---|---|---|
| JP | 11-276572 | 10/1999 | |
| JP | 11-343339 | 12/1999 | |
| JP | 2002-080593 | 3/2002 | |
| JP | 2002-128899 | 5/2002 | |
| KR | WO 2007034795 A1 * | 3/2007 | ............ A61K 8/042 |
| KR | 10-2010-0091945 | 8/2010 | |
| KR | 10-2010-0138189 | 12/2010 | |
| KR | 10-2011-0076826 | 7/2011 | |
| KR | 10-2011-0076838 | 7/2011 | |
| WO | 2006/080523 | 8/2006 | |
| WO | 2007/034795 | 3/2007 | |
| WO | WO 2007034795 A1 * | 3/2007 | |
| WO | 2007/132785 | 11/2007 | |

OTHER PUBLICATIONS

Hiroo Iwata et al. Biomaterial 19 , 1869-1786, Oct. 1998.
Terek M. Shazly et al., Biomaterials 29, 4584-4591, Dec. 2008.
Masao Kunioki et al., vol. 65, Issue 10, pp. 1889-1896, Sep. 6, 1997.
The extended European Search Report, European Patent Office, Jul. 10, 2015, European Patent Application No. 12861883.2.

* cited by examiner

IN SITU CROSSLINKING HYDROGEL COMPRISING γ-POLYGLUTAMIC ACID AND METHOD FOR PRODUCING THE SAME

CROSS-REFERENCE TO RELATED APPLICATIONS

Not Applicable

STATEMENT REGARDING FEDERALLY SPONSORED RESEARCH OR DEVELOPMENT.

Not Applicable

THE NAMES OF THE PARTIES TO A JOINT RESEARCH AGREEMENT.

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB).

Not Applicable

STATEMENT REGARDING PRIOR DISCLOSURES BY THE INVENTOR OR A JOINT INVENTOR.

Not Applicable

BACKGROUND OF THE INVENTION (a) Field of the Invention

This invention relates to a biodegradable, biocompatible hydrogel, which can be used for sealants of suppressing the leakage of blood or air during surgical operation, tissue adhesives, anti-adhesive agents and drug delivery carriers, and a method for producing the same.

(b) Description of the Related Art

Fibrin glues and protein-based adhesives have been mostly used for sealants and adhesives for medical purposes, especially surgical operation. However, the fibrin glues are likely to be detached off from surgical sites due to their quite low adhesive force and also may cause the spread of diseases such as virus infections because they are blood products. As the protein-based adhesives, there have been used products (U.S. Pat. No. 5,385,606, product name: Bioglue®) of using albumin (bovine serum albumin) and glutaraldehyde, and products (product name: GRF Glue®) of using a combination of gelatin, resorcinol and formaldehyde, but they may cause infections due to the use of animals-originated proteins and have poor biocompatibility due to toxic problems of aldehydes which are used as a crosslinking agent.

Lately, in order to replace such blood products or protein products, studies of in situ forming hydrogels using synthetic polymers (usually, polyethylene glycol (PEG)) or carbohydrates (usually, dextran) have been vigorously being conducted and some of them have already been released on the market. Depending on the type of crosslinking reactions, there can be radical polymerization reaction, and nucleophilic and electrophilic substitution reaction. The substitution reaction may be further divided into an imine bond, and an amide bond according to the type of bonds. For an example of radical polymerization, a photo-activated polyethylene glycol (PEG) which is being sold under product name, FocalSeal® (Genzyme), is reported to exhibit higher strength than the fibrin sealants, but it requires a light source and a photo-initiator, and it may cause problems in that blood inhibits its polymerization reaction by preventing the penetration of light sources, and inconvenience for use. The imine bond is to be generated from the reaction of an aldehyde group and an amine group, and it has been reported that aldehyded dextrans are used as electrophiles and chitosan or aminated polyvinyl alcohols (US 2005/00028930), multi amino PEG (US 2006/0078536, Biomaterials 29 (2008) 4584-4591), and ε-polylysine synthesized through microbe culture (WO 2006/080523) are used as nucleophiles. However, the aldehyded dextrans still have toxicity resultant from aldehyde groups and lack of stability issue because they are readily oxidized and thus lose their reactivity. For amide bonding, there have been widely used methods of activating a carboxylic acid to a succinimidyl ester and then of reacting it with an amine group which is nucleophilic. It is reported that mostly, an activated multicarboxylate PEG ester is used as an electrophile, and collagen (U.S. Pat. No. 5,162,430) and serum albumin (U.S. Pat. No. RE38,827), which are natural proteins, are used as a nucleophile, but they still have concerns about the spread of diseases as described above. Moreover, there has been disclosed a hydrogel by crosslinking reaction of multifunctional PEG activated ester with chitosan or methoxy PEG-conjugated chitosan (U.S. Pat. No. 6,602,952), but since its gelation time is two hours or so, it is not suitable for an in situ crosslinking hydrogel. As synthetic nucleophiles, examples of using multiamino-, or multi mercapto-PEG (U.S. Pat. No. 5,874,500, product name CoSeal®) and examples of using trilysine (U.S. Pat. No. 6,566,406, product name DuraSeal®) have been developed and commercialized. As stated above, numerous examples of using polyethylene glycol with excellent biocompatibility have been reported as a synthetic polymer.

γ-Polyglutamic acid, a γ-polypeptide produced by the amide bond of γ-carboxylic acid and α-amino group of glutamic acid, is a water-soluble, anionic, biodegradable, and biocompatible polymer which is biosynthesized by *Bacillus subtilis*, a soybean-fermented food microorganism. Attempts are being made to crosslink γ-polyglutamic acid for use as an absorbent or a hydrogel for medical purpose, and typical examples thereof are as follows.

As methods by ionic bonding, Japanese Patent Laid-Open No. 1999-276572 discloses that a polygamma glutamate complex prepared by hydrogenating quaternary amine salts such as chitosan to carboxylic anions of γ-polyglutamates is used for surgical sutures, wound care dressings, anti-adhesive products, and antihemorrhagics.

As examples of crosslinking by chemical bonding using crosslinking agents, Japanese Patent Laid-Open No. 1999-343339 discloses that γ-polyglutamic acid is crosslinked by use of polyepoxy compounds such as diethyleneglycol diglycidyl ether as a crosslinking agent, and it is applied to anti-adhesive agents in WO 2007/132785. However, since the reaction conditions are 40° C. for 48 hours, or 90° C. for 30 min, it is impossible to apply it for the purpose of in situ gelation in medical fields.

Also, it has been reported that water-soluble carbodiimides are used as a condensate for promoting the reaction of carboxyl groups of γ-polyglutamic acid and nucleophiles. Of them, it has been disclosed in Japanese Patent Laid-Open No. 2002-128899 that the fructose with biodegradability, lysine, chitosan, etc. are used as crosslinking compounds and 3-(3-dimethyl aminopropyl)-1-ethyl carbodiimide (EDC) is used as a water-soluble carbodiimide, but this reaction condition is still too long as 24 hours at a room temperature. Furthermore, it has been disclosed in J. Appl. Polym. Sci. 65, pp 1889-1896, 1997 that γ-PGA-EDC precipitates were produced through the reaction of γ-polyglutamic acid and EDC, followed by the addition of 1,3-propane diamine as a crosslinking agent to prepare a hydrogel. However, this condition is also described to let it stand for one day after mixing and its yield is pretty low as 10% or under.

It has been disclosed in Japanese Patent Laid-Open No. 1997-103479 and Biomaterial 19 (1998) 1869-1876 that when gelatin is reacted with succinimidized α-polyglutamic acid as a crosslinking agent, it is gelated within 30 seconds, but this result suggests that γ-polyglutamic acid merely assists the gelation reaction of gelatins which are naturally gelated at a certain temperature around 40° C., and it does not suggest that γ-polyglutamic acid itself becomes a main ingredient of the hydrogels.

Therefore, there are constant needs of hydrogels with a short gelation time, biocompatibility and biodegradability, and having excellent adhesive force and burst strength so as to be preferably applicable to tissue adhesion.

BRIEF SUMMARY OF THE INVENTION

Under the technical backgrounds as described above, it is an object of the present invention to provide a γ-polyglutamic acid derivative with improved activity in aqueous solutions, and a hydrogel comprising the γ-polyglutamic acid derivatives with tissue adhesive force required for tissue sealants for medical purpose and having biodegradability and bio compatibility.

Further, it is another object of the invention to provide a method of preparing the γ-polyglutamic acid derivative and the hydrogel, a kit for the preparation of the hydrogel, and a tissue adhesive composition comprising components capable of formation of the hydrogel.

The inventors, while studying to fulfill the formation conditions of hydrogels and maintain their activity for a certain period of time in a state of aqueous solution of each material, have found that a hydrogel with tissue adhesive force required for tissue sealants for medical purpose and having biodegradability and biocompatibility could be produced by using the crosslinking reaction of a γ-polyglutamic acid derivative of which mass production is available by the fermentation of microbes, and which is a biosynthetic poly amino acid, possesses at its side chains carboxyl groups of which some are activated, and a polyethylene glycol based polymer which is widely used as a biomaterial and possesses amino groups or thiol groups at its side chains and thus completed the invention. In particular, the activated γ-polyglutamic acid derivative is characterized in that an alkyl group is introduced to the γ-polyglutamic acid so as to minimize activity decrease thereof in its aqueous solutions which is the drawback of the γ-polyglutamic acids directly activated with succinimide groups. (γ-PGA-NHS)

Therefore, in one embodiment of the present invention, there is provided a γ-polyglutamic acid derivative in which its carboxyl group is modified to give alkanoic acid terminal and newly formed carboxyl functional group is activated by an succinimide group to at least some carboxyl groups.

In another embodiment of the invention, there is provided a method of preparing the γ-polyglutamic acid derivative according to one embodiment of the invention, comprising a first step of reacting at least some carboxyl groups of a γ-polyglutamic acid with a lower alkanolamine having 1 to 5 carbon atoms to form a γ-polyglutamic acid-alkanolamine; a second step of reacting a hydroxyl group of the γ-polyglutamic acid-alkanolamine with an anhydride of an acid selected from the group consisting of glutaric acid and succinic acid, or 1-halo alkanoic acid selected from the group consisting of 1-halo valeric acid, 1-halo propionic acid and 1-halo methylcarbonic acid to form an alkanoic acid terminal; and a third step of reacting the thus formed carboxyl terminal with N-hydroxysuccinimide or N-hydroxysulfosuccinimide to form a γ-polyglutamic acid derivative of which at least some carboxyl groups are activated.

In still another embodiment of the invention, there is provided a hydrogel comprising a crosslinked body obtained by crosslinking the γ-polyglutamic acid derivative according to one embodiment of the present invention and a polyethylene glycol based polymer having a plurality of nucleophilic functional groups.

Further, there is provided in another embodiment of the invention a method of preparing a hydrogel, comprising a first step of reacting at least some carboxyl groups of a γ-polyglutamic acid with a lower alkanolamine having 1 to 5 carbon atoms to form a γ-polyglutamic acid-alkanolamine; a second step of reacting a hydroxyl group of the γ-polyglutamic acid-alkanol amine with an anhydride of an acid selected from the group consisting of glutaric acid and succinic acid, or 1-halo alkanoic acid selected from the group consisting of 1-halo valeric acid, 1-halo propionic acid and 1-halo methylcarbonic acid to form an alkanoic acid terminal; a third step of reacting the thus formed carboxyl terminal with N-hydroxysuccinimide or N-hydroxysulfosuccinimide to form a γ-polyglutamic acid derivative of which at least some carboxyl groups are activated; and a fourth step of performing the crosslinking reaction of the thus activated γ-polyglutamic acid derivative and a polyethylene glycol based polymer having a plurality of nucleophilic functional groups.

Further, in still another embodiment of the invention, there are provided a kit for the preparation of a hydrogel and a tissue adhesive composition, comprising the γ-polyglutamic acid derivative according to one embodiment of the invention and a polyethylene glycol based polymer having a plurality of nucleophilic functional groups.

Hereafter, the γ-polyglutamic acid derivatives, the hydrogels, the methods for producing them, and the tissue adhesives according to the embodiments of the invention will be described in detail.

In order to produce a hydrogel with adhesive force, it is desirable that cross-linkage occurs through bonding between polymer chains having at least two functional groups and reacting to each other and at least one of the polymers forms a covalent bond with tissue surface, simultaneously with the crosslinking reaction.

A chemical covalent bond is formed by reaction between an electrophile and a nucleophile, and the electrophilic functional group is adhered to tissues by reacting with an amino group (—NH$_2$), a thiol group (—SH), or a hydroxyl group (—OH) present in collagen components of biological tissue. For such electrophilic functional groups, an aldehyde groups and an activated ester group may be used and for example, in case of the reaction with amino groups, tissue adhesion occurs through an imine bond and an amide bond, respectively, simultaneously with the crosslinking reaction. It has been elucidated that if at least some of γ-polyglutamic acid are activated to convert into succinimide ester groups by reaction with a certain compound, the thus activated γ-polyglutamic acid can quickly gelate (crosslinking reaction) with a polyethylene glycol based polymer having nucleophilic functional groups such as an amine group, thiol group or hydroxyl group at a room temperature to form a hydrogel. Hence, the hydrogels are very suitable to be applied for tissue adhesion because they can be in situ formed in a gel state in medical fields. Further, the activated γ-polyglutamic acid derivative according to a preferred embodiment of the invention is characterized in that an alkyl group is introduced to the γ-polyglutamic acid so as to minimize activity decrease thereof in its aqueous solutions, which is the drawback of the γ-polyglutamic acids directly activated with succinimides.

The thus activated γ-polyglutamic acid derivative having alkanoic acid group can form a hydrogel by quickly gelating with a polyethylene glycol based polymer having a nucleophilic functional group such as an amine group, thiol group or hydroxyl group at a room temperature. Further, the activated γ-polyglutamic acid derivative has enhanced stability in its aqueous solutions by virtue of the addition of alkyl groups, without being required to be used right after dissolution, and it still maintains gelation time, burst strength and adhesion strength at its initial level for two or more hours after dissolution. As the hydrogels having such properties can be adhered to tissues with excellent adhesive force and advantageously applied for the adhesion of biological tissues, it can be effectively used as a tissue sealant for medical purposes.

The γ-polyglutamic acid derivatives and the hydrogels according to such embodiments will be explained in more detail.

The "hydrogels" may be defined to refer to polymer matrix capable of swelling and may have a crosslinked structure including a covalent bond or a non-covalent bond. Further, such hydrogels may have a three dimensional network structure comprising the crosslinked structure and may form elastic gels by absorbing water.

The hydrogels according to one embodiment of the present invention comprise a crosslinked body obtained by crosslinking γ-polyglutamic acid derivatives of which at least some carboxyl groups are activated and polyethylene glycol based polymers having a plurality of nucleophilic functional groups, and the γ-polyglutamic acid derivatives may be those to which succinimide ester derivatives containing alkyl groups are introduced, resulted by introducing lower alkanolamines having 1 to 5 carbon atoms as a linker to at least some carboxyl groups, reacting the introduced hydroxyl terminals of the linker with cyclic alkyl anhydrides to generate carboxyl groups at terminals, and activating them to succinimides.

The lower alkanolamines having 1 to 5 carbon atoms used as a linker, for example, may be aminomethanol, 1-amino-2-propanol, 1-amino-3-propanol, 1-amino-4-butanol, 1-amino-5-pentanol or mono ethanol amine (MEA or 2-aminoethanol) and preferably, they may be mono ethanol amine.

The succinimide ester derivatives may include succinimidyl valerate (SVA: —$CH_2CH_2CH_2CH_2$—CO—NHS), succinimidyl glutarate (SG: —CO—$CH_2CH_2CH_2$—CO—NHS), succinimidyl propionate (SPA: —$CH_2CH_2$—CO—NHS), succinimidyl succinate (SS: —CO—$CH_2CH_2$—CO—NHS), and succinimidyl carboxymethylated (SCM: —$CH_2$—CO—NHS), depending on the kinds of the introduced alkyl groups.

Preferably, the γ-polyglutamic acid derivatives may be those represented by chemical formula 1:

wherein,
a total sum of l, m, and n is an integer of 390 to 15,500,
a ratio of l, m, and n is l:m:n=0 to 0.5:0.2 to 0.5:0.2 to 0.8,
L is a linker, M is each independently H, an alkali metal or alkali earth metal, R is $CH_2$,
b is 0 or 1, and c is an integer of 1 to 5.

The linker is preferably —HN—(R)a-O—, and R contained in the linker is $CH_2$, and a is an integer of 1 to 5.

In chemical formula 1 above, —(CO)b-(R)c-CO— may be preferably —$CH_2CH_2CH_2CH_2$—CO—, —CO—$CH_2CH_2CH_2$—CO—, —$CH_2CH_2$—CO—, —CO—$CH_2CH_2$—CO—, or —$CH_2$—CO—.

The hydrogels can quickly gelate by crosslinking reaction in their aqueous solutions of pH 7.2~11.0, 37° C. that falls under physiological conditions, and in situ gel formation is possible on living organs or tissues of animals or humans. The crosslinking reaction time till they become gels even under such physiological conditions may be within 10 min, preferably within 2 min, and more preferably within 30 sec. Therefore, since the hydrogels can be in situ formed in a gel state in medical fields to be applied to biological tissues, they can be effectively used for tissue adhesion.

A molar ratio of the ester groups of the activated γ-polyglutamic acid derivative among the carboxyl groups of the γ-polyglutamic acid derivative may be preferably 0.10 to 0.99, more preferably 0.30 to 0.80, and most preferably 0.5 to 0.7. With being activated at such molar ratio, the gelation time of the hydrogels can be shortened and adhesive force and strength to biological tissues can be optimized. As the activation level is increased, crosslinking points which form a three dimensional mesh structure of the hydrogels produced by crosslinking reaction are increased as well. Thus, the physical strengths of hydrogels such as compressive strength or tensile strength are increased, and tissue adhesive force is also increased.

Before the activation, γ-polyglutamic acid may be represented by general formula 1:

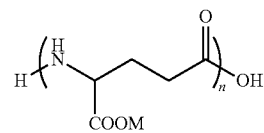

wherein,
n is from 390 to 15,500 and preferably, 3,900 to 7,800, and
M is H, an alkali metal or alkali earth metal (for example, Na, K, Ca, or Mg, and preferably, Na).

A weight average molecular weight of the γ-polyglutamic acid may be preferably 50,000 to 2,000,000 Daltons, more preferably 50,000 to 1,000,000 Daltons.

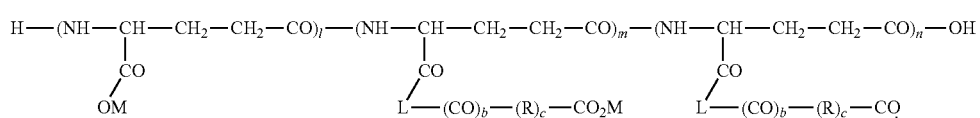
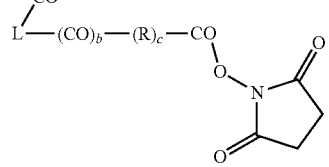

If the molecular weight is too high, the dissolution time is too long so it is inconvenient to use.

The polyethylene glycol based polymers which form a crosslinked body together with the activated γ-polyglutamic acid derivatives according to a preferred embodiments of the invention may be preferably those with an amine group or a thiol group bonded to their terminals. For example, such polyethylene glycol based polymers may have such structure that repeat unit of polyethylene glycols is bonded to each hydroxyl group of dihydric or more, preferably 2 to 12 polyhydric alcohols, and an amine group, thiol group or hydroxyl group is bonded to their terminals. More particularly, such polyethylene glycol based polymers may be represented by chemical formula 2:

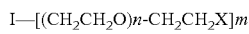

wherein, I is a radical derived from 2 to 12 polyhydric alcohols, where the hydrogen of each hydroxyl group of the polyhydric alcohols is substituted by —(CH$_2$CH$_2$O)n—CH$_2$CH$_2$X and it presents a radical in the form of an ether bond therewith, X represents an amine group, thiol group or hydroxyl group, n is 19 to 170, and m is an integer of 2 to 12, which is equal to the number of the hydroxyl groups of the polyhydric alcohols which I is derived from.

In chemical formula 2 above, specific examples of I may include diols such as ethylene glycol, propandiol, butandiol, pentandiol, hexandiol, etc.; or tri to dodecahydric polyols selected from disaccharides such as glycerol, erythritol, threitol, pentaerythritol, xylitol, adonitol, sorbitol, mannitol, palatinose, maltose monohydrate, or maltitol, or trisaccharides such as D-raffinose pentahydrate. More particularly, the above I may be a radical derived from 4 to 12 polyhydric alcohols.

An example of the polyethylene glycol based polymers falling under the category of chemical formula 2 above may include polymers made by binding a polyethylene glycol repeat unit having terminal nucleophilic functional groups to a radical derived from pentaerythritol or sorbitol, for example, a polymer of chemical formula 3 or 4 below.

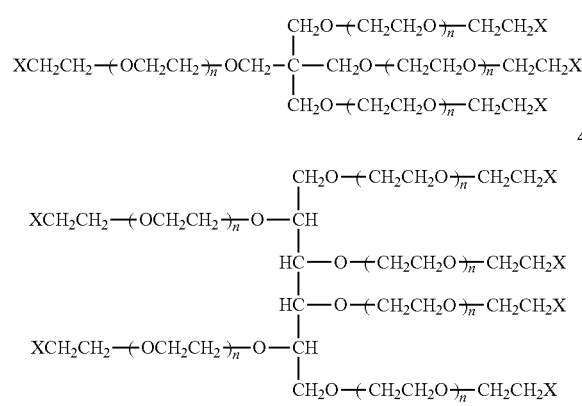

In chemical formulae 3 and 4 above, X and n are as defined in formula 2 above.

Since such polyethylene glycol based polymers contain a lot of nucleophilic functional groups such as amine groups, thiol groups or hydroxyl groups, they can form amide bond, thioamide bond or ester bond, together with the activated γ-polyglutamic acid derivatives of chemical formula 1, and they can form a crosslinked structure therefrom to create a crosslinked body and hydrogel having a three dimensional network structure. In particular, such polyethylene glycol based polymers can perform speedy crosslinking reaction with the activated γ-polyglutamic acid derivatives to provide hydrogels having a short gelation time.

Further, such polyethylene glycol based polymers, which are typical biocompatible polymers among the synthetic polymers, can make a hydrogel containing their crosslinked body show biocompatibility suitable to be applied for tissue adhesion, etc. The polyethylene glycol based polymers may be prepared according to ordinary methods, for example, by performing the addition polymerization of ethylene oxides and polyhydric alcohols and introducing nucleophilic functional groups thereto.

A weight average molecular weight of the polyethylene glycol based polymers may be 5,000 to 30,000 Daltons, particularly 10,000 to 20,000 Daltons. If the weight average molecular weight is too small, a gelation time required for the formation of crosslinked body and hydrogels is increased, or gelation reaction might not occur well. In contrary, if the molecular weight of the polyethylene glycol based polymers is too big, the biodegradability of the crosslinked body and hydrogels may be deteriorated.

In the hydrogels of one embodiment of the invention, the nucleophilic functional groups of the polyethylene glycol based polymers may have a molar ratio of 0.1 to 2.0, particularly 0.2 to 1.0, and more particularly 0.4 to 0.6, with regard to the activated carboxyl groups (for example, succinimide ester groups) of the γ-polyglutamic acid derivatives. With the satisfaction of such molar ratio, the hydrogels may have excellent adhesive force and burst strength with regard to biological tissues, and the crosslinking degree of the hydrogels may be optimized as well. However, if the molar ratio is too low, the strength of the hydrogels may become weak due to small crosslinking points thereof.

Furthermore, according to another embodiment of the invention, there are provided methods of producing the aforementioned γ-polyglutamic acid derivative and a hydrogel where the γ-polyglutamic acid derivative and the polyethylene glycol based polymer are crosslinked.

Preferably, the method may include a first step of reacting at least some carboxyl groups of a γ-polyglutamic acid with a lower alkanolamine having 1 to 5 carbon atoms to form a γ-polyglutamic acid-alkanol amine; a second step of reacting a hydroxyl group of the γ-polyglutamic acid-alkanol amine with an anhydride of an acid selected from the group consisting of glutaric acid and succinic acid, or 1-halo alkanoic acid selected from the group consisting of 1-halo valeric acid, 1-halo propionic acid and 1-halo methylcarbonic acid to form an alkanoic acid terminal; and a third step of reacting the thus formed carboxyl terminal with N-hydroxysuccinimide or N-hydroxysulfosuccinimide to form a γ-polyglutamic acid derivative of which at least some carboxyl groups are activated.

The steps 1 to 3 of forming the γ-polyglutamic acid derivative of which at least some carboxyl groups are activated will be explained with reference to reaction formula 1 below. Reaction formula 1 is one example of producing the γ-polyglutamic acid derivative according to one embodiment of the invention where monoethanolamine (MEA) is used as a linker, and a carboxyl terminal to which an alkyl group is introduced is formed using an anhydride of succinic acid and then activated using NHS.

Reaction Formula 1

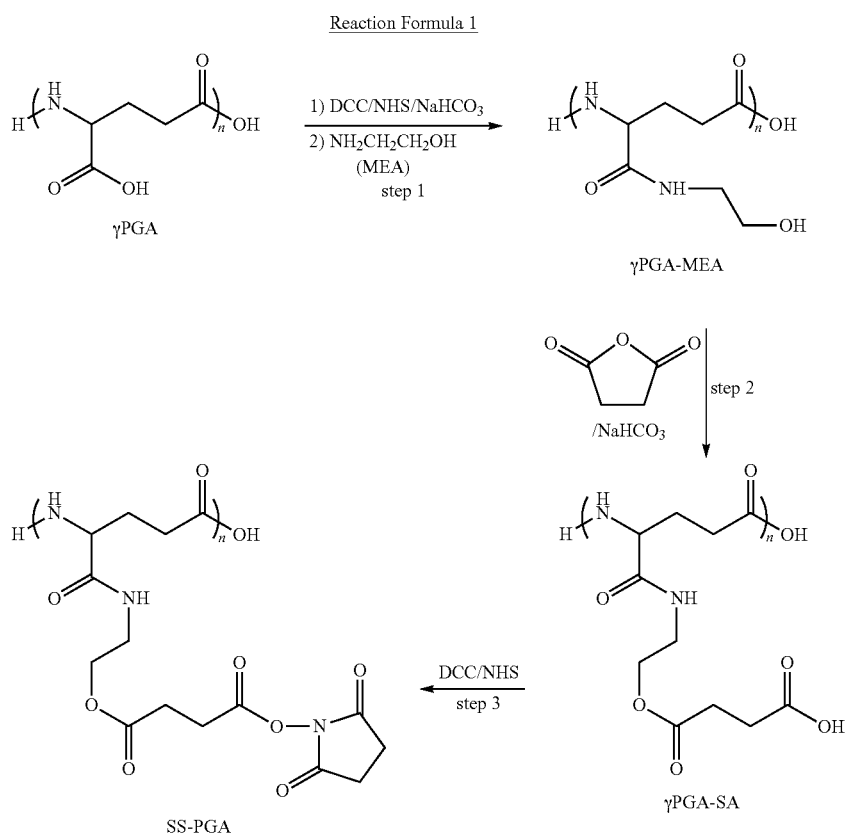

All the reactions in steps 1 to 3 above may be preferably carried out at 0 to 150° C., particularly 20 to 70° C., and for reaction time of 0.5 to 35 hours, preferably 5 to 24 hours.

In the first step, as a step of introducing a linker to the carboxyl groups of γ-polyglutamic acids, the linker may be introduced by reacting at least some carboxyl groups of the γ-polyglutamic acid with a lower alkanolamine having 1 to 5 carbon atoms to form a γ-polyglutamic acid-alkanolamine.

The lower alkanolamine having 1 to 5 carbon atoms may be for example, aminomethanol, 1-amino-2-propanol, 1-amino-3-propanol, 1-amino-4-butanol, 1-amino-5-pentanol, or monoethanolamine (MEA or 2-aminoethanol), and preferably, it may be monoethanolamine.

Preferably, the alkanolamines may be reacted in the presence of carbodiimide type compounds such as DCC and N-hydroxysuccinimide (or N-hydroxysulfosuccinimide), and the carbodiimide type compounds and N-hydroxysuccinimide (or N-hydroxysulfosuccinimide) and alkanolamines may be reacted preferably in a molar ratio of 0.1 to 2, more preferably 1 to 2, respectively, with regard to a mole unit of the carboxyl groups included in the γ-polyglutamic acid prior to the activation.

Preferably, the first step may be conducted in aprotic solvents such as DMSO (dimethyl sulfoxide), DMF (dimethyl formamide), and formamide. It is not desirable to use protic solvents because they may react with activated NHS-esters, or to use other common organic solvents because the reaction materials are insoluble there.

In the second step, as a step of introducing an alkanoic acid terminal, the carboxyl terminal may be formed by reacting a hydroxyl group of the γ-polyglutamic acid-alkanolamine formed in aprotic solvents such as formamide, DMF (dimethyl formamide), and DMSO (dimethyl sulfoxide) with an anhydride of an acid selected from the group consisting of glutaric acid and succinic acid, or by reacting it with 1-halo alkanoic acid selected from the group consisting of 1-halo valeric acid, 1-halo propionic acid and 1-halo methylcarbonic acid.

Preferably, the anhydride of an acid or 1-halo alkanoic acid may be reacted in a molar ratio of 3 to 8, more preferably 4 to 6, with regard to a mole unit of the lower alkanolamines introduced to form the γ-polyglutamic acid-alkanolamines, so as to introduce carboxyl groups to the γ-polyglutamic acid-alkanolamines at 100 mole %.

In the third step, as a step of forming activated γ-polyglutamic acid derivatives, the γ-polyglutamic acid derivatives of chemical formula 1 in which at least some carboxyl groups are activated may be formed by reacting the thus formed carboxyl terminal with N-hydroxysuccinimide or N-hydroxysulfosuccinimide in the presence of carbodiimide type compounds such as dicyclohexylcarbodiimide (DCC).

Preferably, with regard to a mole unit of the carboxyl groups formed through the reaction with the anhydride of an acid or 1-halo alkanoic acid, the carbodiimide type compounds may be added in a molar ratio of 0.1 to 3, more preferably 1 to 2, and N-hydroxysuccinimide or N-hydroxysulfosuccinimide may be added in a molar ratio of 0.1 to 3, more preferably 1 to 2.

The molar ratio of the ester groups of the γ-polyglutamic acid derivatives activated through the third step may be preferably 0.10 to 0.99, more preferably 0.30 to 0.80, and most preferably 0.5 to 0.7, with regard to the carboxyl groups of the γ-polyglutamic acid prior to the activation. With the activation in such molar ratio, the gelation time of hydrogels may be shortened and adhesive force and strength with regard to biological tissues may be optimized.

After the preparation of the activated γ-polyglutamic acid derivatives as described above, they may further be crosslinked with polyethylene glycol based polymers having a plurality of nucleophilic functional groups to produce a crosslinked body and hydrogel.

Hence, according to a preferred embodiment of the present invention, there is provided a method of preparing a hydrogel comprising performing the crosslinking reaction of the γ-polyglutamic acid derivative of chemical formula 1 and a polyethylene glycol based polymer having a plurality of nucleophilic functional groups. According to such preparation method, it is possible to obtain a hydrogel capable of forming a crosslinked structure within fast gelation time even in physiological conditions around a room temperature and in particular, it makes it easy to use such hydrogels for tissue adhesion by applying them for in situ medical treatment.

Particularly, the method of preparing the hydrogel may further comprise, subsequent to conducting steps 1 to 3 of preparing the γ-polyglutamic acid derivative, a fourth step of performing the crosslinking reaction of the activated γ-polyglutamic acid derivatives and the polyethylene glycol based polymers having a plurality of nucleophilic functional groups.

The crosslinking reaction of the fourth step may be conducted in a solution state where the activated γ-polyglutamic acid derivatives and the polyethylene glycol based polymers are mixed. For example, it can be conducted by mixing a first solution containing a solution of the activated γ-polyglutamic acid derivatives and a second solution containing a solution of the polyethylene glycol based polymers.

When combining the first solution and the second solution, it is desirable to mix them in mutually suitable concentrations in order to obtain an even gel. A crosslinking density may be regulated by the concentrations of polymers. As the concentrations of the polymers are increased, the crosslinking density is increased as well. However, in the case of the first solution where the activated γ-polyglutamic acid derivatives having a bigger molecular weight than 1,000 K Dalton, its viscosity starts to increase beyond a certain concentration, making an even mixture difficult. If the concentration of the polymers is too low, the strength of gels is weak or gel formation itself becomes difficult due to a low crosslinking degree thereof.

Hence, the concentration of the polymers, that is, a total concentration of the activated γ-polyglutamic acid derivatives and polyethylene glycol based polymers against the total solutions, may be preferably 1 to 20 wt. %, more preferably 5 to 15 wt. %, and most preferably 8 to 10 wt. %.

Further, a concentration ratio between the activated γ-polyglutamic acid derivatives and the polyethylene glycol based polymers may be preferably 5~10:10~15(wt. %).

As a solvent used for preparing the first solution and the second solution, there may be used a distilled water, and other non-toxic solutions such as buffer solutions including a physiological saline solution, sodium bicarbonate ($NaHCO_3$), boric acid and phosphoric acid.

Of the solvents, the buffer solutions affect gelation time. That is, gelation reaction may or may not occur, or gelation time may be controlled in either fast or slow way, depending on the types of the buffer solutions. The buffer solutions should be prepared using salts having pKa similar to pH of the solid components of the first solution and the second solution, and when they are made in such a manner, their buffering effects could be maximized so as to assist reducing a decrease in the activity of the activated γ-polyglutamic acid derivatives in aqueous solutions.

Preferably, there may be used sodium phosphate buffer as a buffer solution for preparing the first solution. Further, a mixture buffer of sodium phosphate and sodium carbonate may be used to prepare the second solution. The mixture buffer may be those having sodium phosphate and sodium carbonate preferably in a volume ratio of 1:9 to 9:1.

The buffer solution of the first solution may be used preferably at a concentration of 0.01 to 0.3 M, more preferably of 0.05 to 0.1 M, and the buffer solution of the second solution may be used preferably at a concentration of 0.01 to 0.5 M, more preferably of 0.1 to 0.3 M.

The solid components of the first solution and the second solution may be sterilized easily by radiation sterilization, and the sterilization may be performed by radiating preferably a gamma ray of 10 to 50 kGy, more preferably a gamma ray of 20 to 30 kGy. The sterilization treatment may be carried out under such conditions that do not have any adverse effects on gelation time and other physical properties of hydrogels.

When the first solution and the second solution are mixed, amide, thio amide or ester bonds are formed between the activated carboxyl groups (succinimide ester groups, etc.) of the γ-polyglutamic acid derivatives and the nucleophilic functional groups and they become crosslinking points to be able to form a hydrogel having a three dimensional network structure. As a result, the crosslinking reaction may be performed preferably at 0 to 50° C., more preferably 25 to 40° C., and the crosslinking reaction (gelation) may start to occur within 1 sec. to 200 sec., preferably 2 sec. to 100 sec., and more preferably 3 sec. to 50 sec. from the mixture thereof.

However, if the gelation time is 2 sec. or less, it may make smooth application difficult due to the clogs of injection needles or spray tips, and because time is not sufficient to mix each component, uneven gels may be formed, or the formation of covalent bonds to tissue surface may be difficult, thereby causing a low adhesive force. In contrary, if the gelation time is too prolonged, it may not be easy to apply it because it may run in the form of solutions prior to the formation of gel at application sites. Hence, it is desirable to have 3 sec. or more, particularly not less than 5 sec. and not more than 15 sec. in order to maintain high adhesive force and burst strength till penetrating into biological tissue.

Since the hydrogels have excellent properties through rapid gelation even under physiological conditions as explained above, they can be advantageously applied for tissue adhesion, etc. in medical fields. This application may be done by using devices such as a double barrel syringe, but not limited thereto.

The hydrogels prepared by the above methods may be provided in forms of sponge or sheet, or powders by conducting lyophilization, and they may be employed in such forms for anti-adhesive agents, absorbents, drug delivery, etc. Moreover, a kit or a composition containing each component for the formation of hydrogels (the activated γ-polyglutamic acid derivatives of chemical formula 1 and the polyethylene glycol based polymers) may be applied for the adhesion of biological tissue by performing crosslinking reaction and thus forming a hydrogel in situ at medical fields, which will be explained later in detail. For the application to tissue adhesion, a mixture containing the activated γ-polyglutamic acid derivatives and the polyethylene glycol polymers, for example, a mixture aqueous solution is formed on biological tissue and then, the thus formed aqueous solution is subject to crosslinking reaction to form a hydrogel, which can form coatings on the biological tissue.

According to another embodiment of the invention, there is provided a kit for the preparation of the aforementioned hydrogels. This kit for the preparation of the hydrogels may comprise the γ-polyglutamic acid derivatives of chemical formula 1 of which at least some carboxyl groups are activated and the polyethylene glycol based polymers having a plurality of nucleophilic functional groups, as described above.

As explained above, the hydrogels according to one embodiment may be obtained at a rapid gelation rate even under physiological conditions. Such hydrogels, in the form of a kit or a composition prior to gelation thereof comprising each component for the formation thereof, may be applied for tissue adhesion, etc. For example, after the kit or composition comprising each component is applied to biological tissues, gelation occurs on the biological tissue to be able to form a hydrogel and exhibit the function of tissue adhesion. For such applications, a kit according to another embodiment may be used.

According to specific examples, the kit for the preparation of hydrogels may include a first solution containing an aqueous solution of the activated γ-polyglutamic acid derivatives and a second solution containing an aqueous solution of the polymers having nucleophilic functional groups. The kit may be used by mixing the aqueous solutions of the first solution and the second solution and especially, it is characterized by having adhesive force to tissues by mixing the first solution and the second solution and in-situ forming hydrogel.

When such a two-solution reaction type sealant is to be used, mixing and use of the first solution and the second solution may be carried out by several methods. For example, mixing may be carried out by applying one of the concentrates of the first solution and the second solution to the surface of an object to be coated and continuously applying the other, or it may be carried out by mixing the first solution and the second solution in an applicator such as a double barrel syringe and then applying them. If desired, it may be used for anti-adhesion purpose as a sheet consisting of a gel state resin in addition to the use as a sealant. A mixture ratio (volume ratio) of the first solution and the second solution is usually set as 0.5 to 2.0 (the ratio of the second solution against the first solution; its reverse rate is the same).

According to another embodiment of the invention, there is provided a tissue adhesive composition using the hydrogels described in the above. As explained in the above, the hydrogels may be used preferably for biological tissue adhesion, in the form of a composition prior to gelation thereof, comprising each component for the formation thereof. Hence, one embodiment of the tissue adhesive composition may comprise each component for the preparation of hydrogel, for example, the γ-polyglutamic acid derivative of chemical formula 1 of which at least some carboxyl groups are activated and the polyethylene glycol based polymer having a plurality of nucleophilic functional groups.

The composition of one embodiment comprising the γ-polyglutamic acid derivative of which at least some carboxyl groups are activated and the polyethylene glycol based polymer having a plurality of nucleophilic functional groups may be applied into body at a temperature range of 25 to 40° C., for example, near physiological conditions, and when they are being mixed, gelation may occur within 10 min., particularly within 2 min., and more particularly within 5 to 30 sec. to form a hydrogel. Hence, since such compositions may be gelated within a short time after applied to biological tissues, and then adhered to the tissues, preferably, in situ application thereof in medical fields is possible.

Since the methods of applying the tissue adhesive compositions are the same as explained in the kit for the preparation of hydrogels, no further description thereof will be given.

The tissue adhesive compositions may be applied for various applications such as topical wound suture, gastroenterostomy, vascular anastomosis, and ophthalmology surgery.

Since the γ-polyglutamic acid derivatives prepared using the same according to the present invention can maintain their activities in their aqueous solution state for a certain time, the solutions do not need to be used right away after the preparation thereof. They can form gels instantly at wound area, have excellent adhesive force to biological tissues, thereby suppressing the leakage of blood or air, are degradable in living body and thus either absorbed or secreted, and have no toxicity to living body. Furthermore, gelation time can be also controlled and regulated to a desired level.

Therefore, the hydrogels can be advantageously used for various applications including biological tissue adhesion.

BRIEF DESCRIPTION OF THE SEVERAL VIEWS OF THE DRAWING(S)

DETAILED DESCRIPTION OF THE INVENTION

Figure 1:
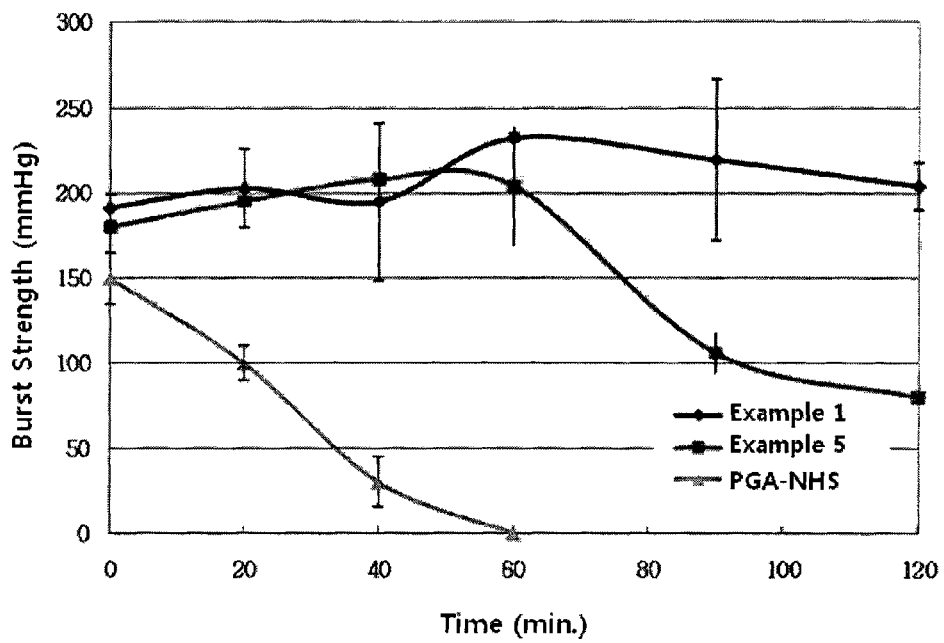
FIG. 1 is a graph showing the stability of the activated γ-polyglutamic acid derivatives in aqueous solutions through the burst strength change of gels according to the lapse of time after dissolution.

Hereafter, the invention will be explained in more detail through examples. However, it is noted that these examples are intended to merely illustrate the invention, and the scope of the invention is not construed to be limited to the examples.

PREPARATION EXAMPLE 1

Preparation of Activated SS-PGA

PREPARATION EXAMPLE 1.1

Preparation of γ-PGA-MEA by Introduction of Linker to γ-PGA

To a dried 1000 ml 2-neck round glass flask were added 100 mmol (12.9 g) of γ-polyglutamic acid (PGA, molecular weight 50K, 500K, 1000K, and 2000K Da) on the basis of carboxyl units and 650 ml of dimethylsulfoxide (DMSO), which were then stirred at 60° C. for 16 hours so that they were evenly dissolved and then, the temperature of the reaction solution was lowered to a room temperature (25° C.). N-hydroxysuccinimide (NHS) and dicyclohexylcarbodiimide (DCC) were measured in 2 equivalent overweights, respectively with regard to the carboxyl units of γ-polyglutamic acid, and sodium bicarbonate was measured in the same molar ratio as γ-polyglutamic acid and then, they were added and stirred under a reduced pressure to eliminate moisture. After one hour, they were reacted under nitrogen atmosphere for 3 hours. After the completion of the reaction, monoethanolamine (MEA) measured in 2 equivalent overweights with regard to the carboxyl units of γ-polyglutamic acid was added and then reacted for 1 hour.

After the completion of the reaction, the reaction solution was filtrated and at the same time, precipitated in 4 L of ethyl acetate (EA) to eliminate sodium bicarbonate and the produced urea. After the complete elimination of the unreacted NHS and DCC by washing twice with EA, they were dried in a vacuum oven for 16 hours or more so as to eliminate residual solvents. Thus, γ-polyglutamic acid (γPGA-MEA) compounds to which the linker was introduced were finally obtained.

PREPARATION EXAMPLE 1.2

Preparation of S-PGA (Succinylated PGA) by Introduction of Alkanoic Acid Group at Linker Terminal To a dried 1000 ml 2-neck round glass flask were added 100 mmol (18.3 g) of γ-PGA-MEA prepared in Preparation Example 1.1 above on the basis of hydroxyl units and 450 ml of dimethylsulfoxide (DMSO), which were then stirred at a room temperature (25) for 2 hours so that they were evenly dissolved and then, succinic anhydride (SA) was measured in 6 equivalent overweights with regard to the hydroxyl units of γ-PGA-MEA, and sodium bicarbonate was measured in a ½ level with regard to the moles of SA and then, they were added and stirred under a reduced pressure to eliminate moisture. After one hour, they were reacted under nitrogen atmosphere for 24 hours.

After the completion of the reaction, the reaction solution was filtrated to eliminate sodium bicarbonate and then, precipitated in 2.7 L of ethyl acetate (EA). After the complete elimination of the unreacted SA by washing twice with EA, they were dried in a vacuum oven for 16 hours or more so as to eliminate residual solvents.

PREPARATION EXAMPLE 1.3

Preparation of Activated SS-PGA (Succinimidyl Succinyl PGA)

To a dried 1000 ml 2-neck round glass flask were added 100 mmol (27.28 g) of S-PGA prepared in Preparation Example 1.2 above on the basis of carboxyl units and 700 ml of dimethylsulfoxide (DMSO), which were then stirred at a room temperature (25° C.) for 2 hours so that they were evenly dissolved and then, N-hydroxysuccinimide (NHS) and dicyclohexylcarbodiimide (DCC) were measured in molar ratios described in Table 1 below, respectively with regard to the mole unit of the carboxyl groups formed through the reaction of SA and then, they were added and stirred under a reduced pressure to eliminate moisture. After one hour, they were reacted under nitrogen atmosphere for 24 hours.

After the completion of the reaction, the reaction solution was filtrated to eliminate the produced urea and then, precipitated in 5.6 L of ethyl acetate (EA). After the complete elimination of the unreacted NHS and DCC by washing twice with EA, they were dried in a vacuum oven for 3 hours and then dried again for 72 hours at a temperature which was increased to 60° C., so as to eliminate residual solvents. Thus, activated SS-PGA ester compounds were finally obtained.

PREPARATION EXAMPLE 2

Preparation of Activated SG-PGA

PREPARATION EXAMPLE 2.1

Preparation of G-PGA (Glutarylated PGA)

To a dried 1000 ml 2-neck round glass flask were added 100 mmol (18.3 g) of γ-PGA-MEA prepared in Preparation Example 1.1 above on the basis of hydroxyl units and 450 ml of dimethylsulfoxide (DMSO), which were then stirred at a room temperature (25° C.) for 2 hours so that they were evenly dissolved and then, glutaric anhydride (GA) was measured in 6 equivalent overweights with regard to the hydroxyl units of γ-PGA-MEA, and sodium bicarbonate was measured in a ½ level with regard to the moles of GA and then, they were added and stirred under a reduced pressure to eliminate moisture. After one hour, they were reacted under nitrogen atmosphere for 24 hours.

After the completion of the reaction, the reaction solution was filtrated to eliminate sodium bicarbonate and then, precipitated in 2.7 L of ethyl acetate (EA). After the complete elimination of the unreacted GA by washing twice with EA, they were dried in a vacuum oven for 16 hours or more so as to eliminate residual solvents.

PREPARATION EXAMPLE 2.2

Preparation of Activated SG-PGA (Succinimidyl Glutaryl PGA)

To a dried 1000 ml 2-neck round glass flask were added 100 mmol (27.28 g) of G-PGA prepared in Preparation Example 2.1 above on the basis of carboxyl units and 700 ml of dimethylsulfoxide (DMSO), which were then stirred at a room temperature (25° C.) for 2 hours so that they were evenly dissolved and then, N-hydroxysuccinimide (NHS) and dicyclohexylcarbodiimide (DCC) were measured in molar ratios described in Table 1 below, respectively with regard to the mole unit of the carboxyl groups formed through the reaction of GA and then, they were added and stirred under a reduced pressure to eliminate moisture. After one hour, they were reacted under nitrogen atmosphere for 24 hours.

After the completion of the reaction, the reaction solution was filtrated to eliminate the produced urea and then, precipitated in 5.6 L of ethyl acetate (EA). After the complete elimination of the unreacted NHS and DCC by washing twice with EA, they were dried in a vacuum oven for 3 hours and then dried again for 72 hours at a temperature increased to 60° C. so as to eliminate residual solvents. Thus, activated SG-PGA ester compounds were finally obtained.

EXPERIMENTAL EXAMPLE 1

Measurement of Content of Substituted NHS

Figure 4:
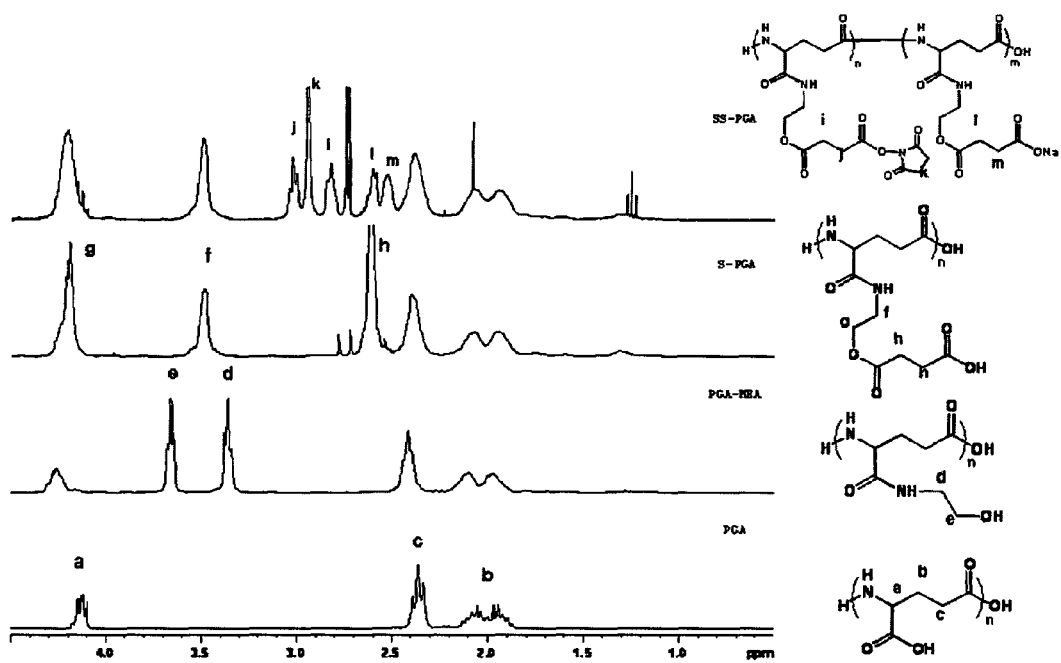
FIG. 4 shows $^1$H NMR spectrum with regard to the content of substituted NHS within the activated SS-PGA according to Experimental Example 1 of the invention.
Figure 5:
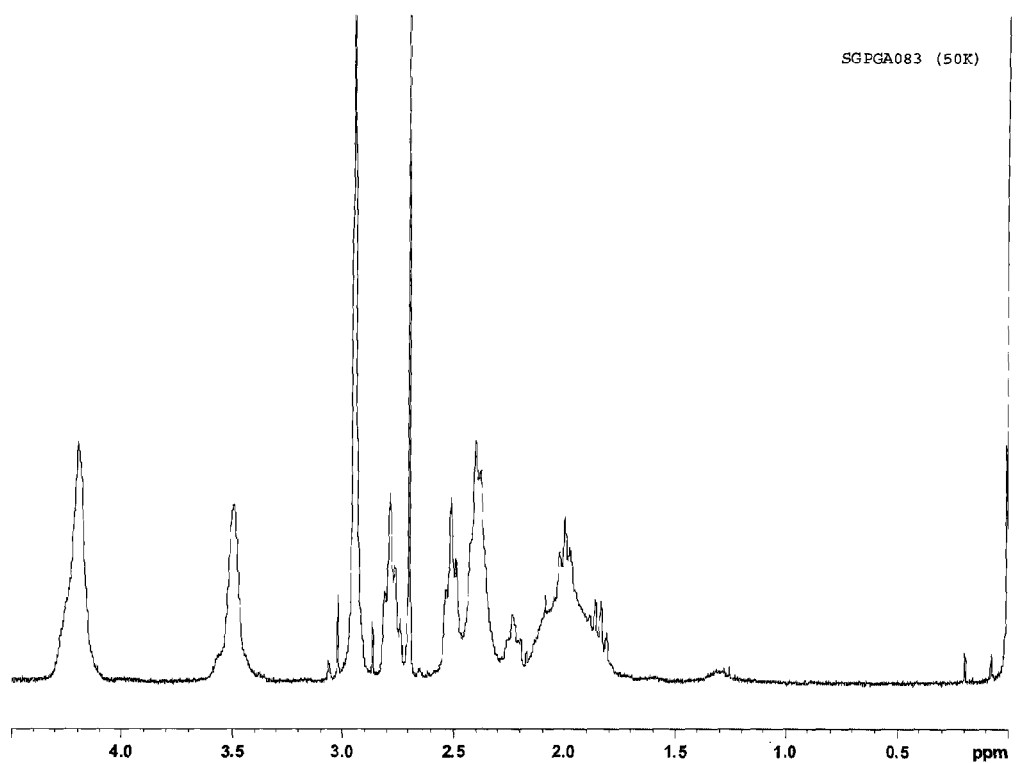
FIG. 5 shows $^1$H NMR spectrum with regard to the content of substituted NHS within the activated SG-PGA according to Experimental Example 1 of the invention.

The contents of substituted NHS within the activated SS-PGA and the activated SG-PGA prepared according to Preparation Examples 1 and 2 above were measured using NMR and illustrated in Table 1 below and FIG. 4 (SS-PGA) and FIG. 5 (SG-PGA). In particular, it was obtained as a ratio of the integral value of —$CH_2$— (2.8 ppm) of bonded N-hydroxysuccinimide (NHS) with regard to the integral value of —$CH_2$-(2.05 ppm) of γ-PGA measured in $^1$H NMR (D2O solvent).

TABLE 1

NHS Introduction Ratio of γ-PGA According to Input of NHS and DCC

| No. | γ-PGA Weight Average Molecular Weight (kDa) | [NHS]/ [COOH] | [DCC]/[COOH] | Content of Substituted NHS (mole %) |
|---|---|---|---|---|
| T-1 | 50 | 2.0 | 2.0 | 65 |
| T-2 | 1,000 | 1.0 | 1.0 | 35 |
| T-3 | 1,000 | 1.5 | 1.5 | 53 |
| T-4 | 1,000 | 2.0 | 2.0 | 64 |
| T-5 | 1,000 | 3.0 | 3.0 | 81 |
| T-6 | 1,000 | 4.0 | 4.0 | 84 |

With reference to Table 1 above, when reaction was performed for 24 hours at room temperature, the substitution degree of NHS increased in proportion to the amounts of NHS and DCC, regardless of the weight average molecular weight of γ-PGA. However, only 80 mole % or so of the total carboxyl groups were substituted even when excess amounts of NHS and DCC more than 3 equivalents with regard to carboxyl groups were reacted.

EXAMPLES 1 to 6

Preparation of Hydrogels According to Concentrations of Activated γ-Polyglutamic Acid Derivatives and Polyethylene Glycol Based Polymers The activated γ-polyglutamic acid derivatives (SS-PGA) synthesized pursuant to the conditions of T-1 of Table 1 and 4-arm PEG-SH having a molecular weight of 20 kDa were subject to crosslinking reaction (Examples 1 to 3). Further, SS-PGA synthesized pursuant to the conditions of T-4 of Table 1 and 4-arm PEG-SH having a molecular weight of 20 kDa were subject to crosslinking reaction (Examples 4 to 6).

SS-PGA aqueous solution (first solution) was formulated by dissolving SS-PGA in 1 ml of 0.05 M sodium phosphate aqueous solution according to the amounts set forth in Table 2. Similarly, 4-arm PEG-SH aqueous solution (second solution) was formulated by dissolving 4-arm PEG-SH in 1 ml of 0.3 M sodium phosphate/sodium carbonate mixture (5:5) aqueous solution according to the amounts set forth in Table 2. Each 0.5 ml of the first solution and the second solution were collected into a syringe of 1 ml volume. Two syringes were equipped to a dual barrel syringe so that they could be preliminarily mixed in a spray.

TABLE 2

Crosslinking Reaction Conditions of SS-PGA (Buffer Solution: 0.05M Sodium Phosphate Aqueous Solution) and Polyethylene Glycol based Polymer (Buffer Solution: 0.3M P/C Mixture Aqueous Solution)

| No. | Weight Average Molecular Weight of γPGA (kDa) | Concentration of SS-PGA (First Solution) (%) | Polyethylene Glycol based Polymer Type | Molecular Weight (kDa) | Concentration of Polyethylene Glycol based Polymer (Second Solution) (%) |
|---|---|---|---|---|---|
| Ex. 1 | 50 | 7 | 4-PEG-SH | 20 | 12 |
| Ex. 2 | 50 | 7 | 4-PEG-SH | 20 | 10 |
| Ex. 3 | 50 | 6 | 4-PEG-SH | 20 | 10 |
| Ex. 4 | 1000 | 8 | 4-PEG-SH | 20 | 12 |
| Ex. 5 | 1000 | 10 | 4-PEG-SH | 20 | 10 |
| Ex. 6 | 1000 | 12 | 4-PEG-SH | 20 | 10 |

EXAMPLES 7-16

Preparation of Hydrogels According to Types of Polyethylene Glycol Based Polymers The activated γ-polyglutamic acid derivatives (SS-PGA) synthesized pursuant to the conditions of T-4 of Table 1 and polyethylene glycol based polymers were subject to crosslinking reaction. SS-PGA aqueous solution (first solution) was formulated by dissolving SS-PGA in 1 ml of 0.05 M sodium phosphate aqueous solution according to the amounts set forth in Table 3. Similarly, an aqueous solution (second solution) was formulated by dissolving polyethylene glycol based polymers in 1 ml of 0.3 M sodium phosphate/sodium carbonate mixture aqueous solution according to the amounts set forth in Table 3. Each 0.5 ml of the first solution and the second solution were collected into a syringe of 1 ml volume. Two syringes were equipped to a dual barrel syringe so that they could be preliminarily mixed in a spray.

TABLE 3

Crosslinking Reaction Conditions of SS-PGA (Buffer Solution: 0.05M Sodium Phosphate Aqueous Solution) and Polyethylene Glycol based Polymer (Buffer Solution: 0.3M P/C Mixture Aqueous Solution)

| No. | Weight Average Molecular Weight of γPGA (kDa) | Concentration of SS-PGA (First Solution) (%) | Polyethylene Glycol based Polymer Type | Molecular Weight (kDa) | Concentration of Polyethylene Glycol based Polymer (Second Solution) (%) |
|---|---|---|---|---|---|
| Ex. 7 | 1000 | 10 | 2-PEG-NH$_2$ | 10 | 10 |
| Ex. 8 | 1000 | 10 | 2-PEG-NH$_2$ | 20 | 10 |
| Ex. 9 | 1000 | 10 | 4-PEG-NH$_2$ | 20 | 10 |
| Ex. 10 | 1000 | 12 | 4-PEG-NH$_2$ | 20 | 10 |
| Ex. 11 | 1000 | 12 | 4-PEG-SH | 10 | 6 |
| Ex. 12 | 1000 | 12 | 4-PEG-SH | 10 | 1 |
| Ex. 13 | 1000 | 12 | 6-PEG-SH | 10 | 2 |

TABLE 3-continued

Crosslinking Reaction Conditions of SS-PGA (Buffer Solution: 0.05M Sodium
Phosphate Aqueous Solution) and Polyethylene Glycol based Polymer
(Buffer Solution: 0.3M P/C Mixture Aqueous Solution)

| No. | Weight Average Molecular Weight of γPGA (kDa) | Concentration of SS-PGA (First Solution) (%) | Polyethylene Glycol based Polymer Type | Molecular Weight (kDa) | Concentration of Polyethylene Glycol based Polymer (Second Solution) (%) |
|---|---|---|---|---|---|
| Ex. 14 | 1000 | 10 | 6-PEG-SH | 10 | 2 |
| Ex. 15 | 1000 | 12 | 6-PEG-SH | 20 | 4 |
| Ex. 16 | 1000 | 12 | 6-PEG-SH | 20 | 8 |

EXPERIMENTAL EXAMPLE 2

Measurement of Gelation Time 0.5 ml of the first reaction solution and the second reaction solution prepared according to Examples 1 to 16 were each collected into a 1 ml syringe and then, the two solutions were mixed using a magnetic stirrer in a 24 well cell culture plate made of clear polystyrene. They were stirred using a stirring bar having a diameter of 4 mm and a length of 12 mm, at a rate of 500 rpm at a room temperature, and time immediately after the first reaction solution and the second reaction solution were added until the stirring bar stopped was measured using a stop watch. The results are shown in Table 4.

TABLE 4

Gelation Time of SS-PGA and Polyethylene Glycol Derivatives

| No. | Gelation Time (sec.) |
|---|---|
| Ex. 1 | 5 |
| Ex. 2 | 7 |
| Ex. 3 | 7 |
| Ex. 4 | 8 |
| Ex. 5 | 5 |
| Ex. 6 | 2 |
| Ex. 7 | N/G |
| Ex. 8 | N/G |
| Ex. 9 | 4 |
| Ex. 10 | 5 |
| Ex. 11 | 4 |
| Ex. 12 | 30 |
| Ex. 13 | 25 |
| Ex. 14 | 21 |
| Ex. 15 | 10 |
| Ex. 16 | 1 |

The crosslinking reactions of the activated γ-polyglutamic acid derivatives and the polyethylene glycol based polymers did not show a big difference in gelation time regardless of the molecular weights of γ-polyglutamic acids because the substitution degrees of NHS were similar, and they had gelation time of 5 seconds or so. Under the identical conditions, as the concentration of the total polymers was increased, gelation time was decreased.

Moreover, in Example 7 and Example 8 where 2-PEG-NH$_2$ was used as a polyethylene glycol based polymer, no gelation reaction occurred regardless of the molecular weight of PEG within 10 min. Furthermore, in Examples 13 to 16 where crosslinking reaction was performed with regard to 6-arm PEG-SH, because reaction groups per PEG unit are more than 4-arm PEG-SH, rapid gelation occurred at a relatively low concentration. However, if the concentration of 6-arm PEG-SH was increased, gels were unevenly formed due to too fast gelation, as discussed above.

EXPERIMENTAL EXAMPLE 3

Measurement of Burst Strength

The measurement of burst strength was carried out by methods set forth in ASTM2392. 0.35 ml of the first reaction solution and the second reaction solution prepared according to Examples 1 to 16 were each collected into a 1 ml syringe. A collagen casing was washed twice in water and ethanol respectively to eliminate glycerin that was smeared on the collagen casing and then, it was cut to 3×3 cm and punched a hole of 3 mm using a punch for skin biopsy, so as to be used as a tissue replacement product. Thereafter, the collagen casing having a hole of 3 mm was fixed using teflon as a support. After that, 0.3 ml of the first reaction solution and the second reaction solution were each mixed using a dual barrel syringe to render the volume of the reaction solution to be 0.6 ml, which was then applied to the hole of the collagen casing and let stay for 5 min to be hardened. Then, after the collagen casing to which the mixture reaction solution was applied was separated from the teflon support, it was fixed to a burst strength measuring machine manufactured by the methods set forth in ASTM2392. A hydraulic pressure measured when the hardened gels were broken was used as burst strength. Further, for comparison purpose, the identical test was carried out with regard to fibrin glue (Beriplast®, CSL Behring). The burst strength results of the hydrogels are shown in Table 5.

TABLE 5

Burst Strength of SS-PGA and Polyethylene Glycol Derivatives

| No. | Burst Strength (mmHg) |
|---|---|
| Ex. 1 | 191.5 |
| Ex. 2 | 180 |
| Ex. 3 | 165 |
| Ex. 4 | 105 |
| Ex. 5 | 180 |
| Ex. 6 | 137 |
| Ex. 7 | N/G |
| Ex. 8 | N/G |
| Ex. 9 | 240 |
| Ex. 10 | 220 |
| Ex. 11 | 118 |
| Ex. 12 | 58 |
| Ex. 13 | 80 |
| Ex. 14 | 84 |
| Ex. 15 | 148 |
| Ex. 16 | 30 |
| Beriplast ® | 105 |

A. Effects According to Concentrations of γ-Polyglutamic Acid Polymers

The maintenance of burst strength up to a certain level is affected by the concentrations of the activated γ-polyglutamic acid polymers. In Examples 2, 3, 5, and 6 where identical 4-arm PEG-SH polymers were used at various concentrations, as the concentrations of γ-PGA polymers were increased, their burst strength were increased as well. However, if the concentration of γ-PGA polymers was 10% or higher, the burst strength didn't increase further and moreover, if it was 12%, its burst strength was rather reduced. This is because too high concentration of the polymers led to an increase in viscosity and consequently, the first solution and the second solution failed to form a uniform gel when mixed.

Also, when the total concentration of the polymers was 9 to 10%, it showed the highest burst strength.

Furthermore, even though the total concentration of the polymers became 10% or so by increasing the concentration of 4-arm PEG-SH polymers, the burst strength was measured low if the concentrations of γ-polyglutamic acid polymers were lowered to 6% with regard to molecular weight 50K, or to 8% or under with regard to 1000K (see Examples 3 and 4).

B. Effects According to Concentrations of Polyethylene Glycol Based Polymers

In Examples 1 and 2 and Examples 11 and 12, when the hydrogels were produced only by varying the concentrations of the polyethylene glycol based polymers under the same conditions, their burst strength were increased in proportion to the concentrations of the polyethylene glycol based polymers.

When 6-PEG-SH was used as a polyethylene glycol based polymer, since it has more reaction groups per PEG unit than 4-arm PEG-SH, it could form a uniform gel at a lower concentration, but the total concentration of the total polymers was low, thereby causing fewer crosslinking points and thus, it showed a lower burst strength than the gelation reaction with 4-arm PEG-SH. Moreover, if the concentration of 6-arm PEG-SH was too high (Example 16), a very low burst strength was measured because uneven gel was formed due to too quick gelation of no longer than 1 second and in contrary, if the concentration is too low, it caused to form a weak gel due to insufficient crosslinking points.

C. Effects According to Types of Polymers

In Examples 5 and 9 and Examples 6 and 10 where the concentrations of γ-PGA and polyethylene glycol polymers and the molecular weight of γ-PGA were the same and the types of the polyethylene glycol based polymers were varied as 4-PEG-SH and 4-PEG-NH$_2$, respectively, Examples 9 and 10 prepared by using 4-PEG-NH$_2$ showed a higher burst strength than Examples 5 and 6 where 4-PEG-SH was used. Besides, they had the highest burst strength among the whole hydrogels according to Examples 1 through 16.

However, as discussed in A, in case of Examples 6 and 10 where the concentration of γ-PGA was 12%, they showed lower burst strengths than Examples 5 and 9 where the concentration of γ-PGA was 10%. This is because too high concentration of the polymers led to an increase in viscosity and consequently, the first solution and the second solution failed to form a uniform gel when mixed.

EXPERIMENTAL EXAMPLE 4

Measurement of Adhesion Strength

A fatty layer of the pig skin was removed using a scalpel and the skin was cut to 1×5 cm. Using dual barrel syringe, each 0.10 ml of the first and second solution was applied to one dermal side of pig skin. Immediately the other sample of skin was placed on the first layer to achieve bonding area of 1×1 cm$^2$. The weight of 50 g was applied thereto and allowed to stay for 10 min so that the gel became hardened. After 10 min. passed, the weight was removed and then, shear force was given to the coupled pig skin or collagen casing at a rate of 100 mm/min. using a tensile tester (H5K-T, Hounsfield Co.) until they were separated from each other. A loaded weight when separation is occurring is defined as adhesion strength. Further, for comparison purpose, the identical test was carried out with regard to fibrin glue (Beriplast®, CSL Behring). The adhesion strength results of the hydrogels are shown in Table 6.

TABLE 6

Adhesion Strength of SS-PGA and Polyethylene Glycol Derivatives

| No. | Adhesion Strength (gf/cm$^2$) |
|---|---|
| Ex. 5 | 398 |
| Ex. 6 | 148 |
| Ex. 10 | 238 |
| Ex. 14 | 65 |
| Ex. 15 | 196 |
| Beriplast ® | 92 |

The adhesion strength showed a pattern similar to the burst strength. When gelation time is 5 sec. or so, gelation between the two materials occurred and at the same time, they were bonded to the collagen casing and thus, adhesion strength of about 400 gf/cm$^2$ was measured. However, if gelation was too fast, adhesion strength was measured low because there wasn't sufficient time to be bonded to collagen casing.

EXPERIMENTAL EXAMPLE 5

Pot Life Test in Aqueous Solution

The pot life of SS-PGA in aqueous solutions was tested by measuring burst strength according to time lapse after its dissolution. After dissolution of SS-PGA, its solution was stayed at room temperature for a predetermined time.

The burst strengths were measured in an interval of 20 min. up to 2 hours right after the preparation of the first reaction solution, and the pot life results of SS-PGA in buffer are shown in FIG. 1.

As shown in FIG. 1, the pot life of SS-PGA according to Examples 1 and 5 in aqueous solutions was remarkably enhanced, compared to the γ-polyglutamic acid directly activated with succinimide groups (γ-PGA-NHS produced according to Preparation Example T-12 of Korean Patent Application No. 10-2010-0138189 by the same inventors (PGA molecular weight 1,000K, ([NHS]/[COOH]=1.2, [DCC]/[COOH]=1.5, reaction time 3 hours)). In case of the PGA-NHS in aqueous solutions, NHS was rapidly deactivated and burst strength of its hydrogel was reduced to 30 mmHg in 40 min., which was 20% of the initial level (150 mmHg), while SS-PGA of Example 1 kept its activity for 2 hrs.

EXPERIMENTAL EXAMPLE 6

Elastic Modulus of Hydrogels

Elastic modulus (or storage modulus) of the hydrogels prepared in Example 1 above with regard to their shear rate was measured using a rheometer (ARES-G2, TA Instrument Co). 0.7 ml of the first reaction solution and the second reaction solution were each applied to a plate of the rheometer (diameter 2 cm, interval 1.13 mm) using a dual barrel syringe equipped with an injection needle at its ejection port so that there were no empty space and then, they were allowed to stay for 5 min at a room temperature to be hardened. Under the conditions of 20% of strain rate, when storage modulus was measured at shear rates from 0.10 rad/sec increased to 100 rad/sec, it exhibited storage modulus of $1.03*10^5$ dyne/cm$^2$ at a low shear rate of 0.10 rad/sec and 1.12 dyne/cm$^2$ at a high shear rate of 100 rad/sec.

EXPERIMENTAL EXAMPLE 7

Swelling Test

Figure 2:
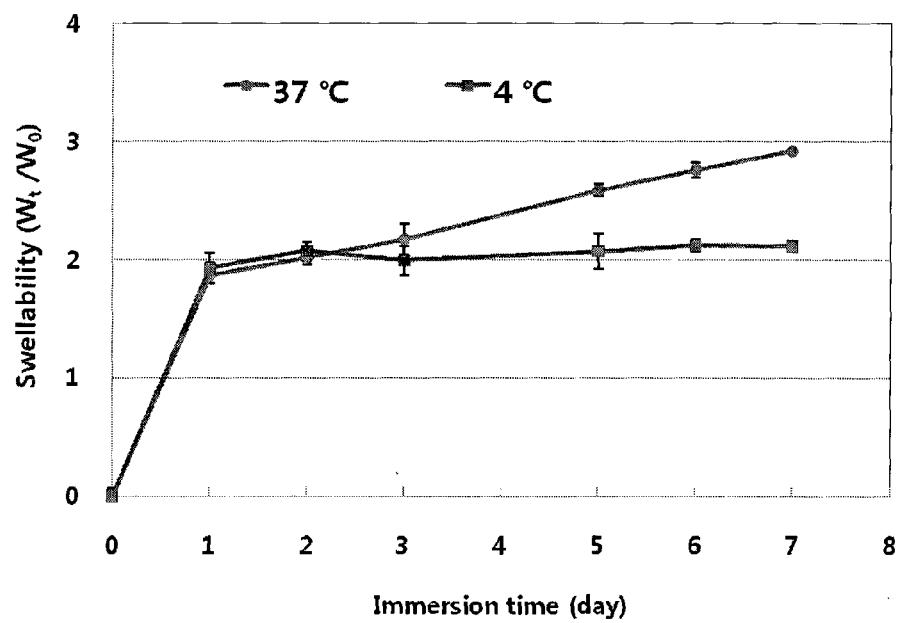
FIG. 2 is a graph showing the swellability of the hydrogel prepared by the crosslinking reaction of the activated γ-polyglutamic acid derivative and the polyethylene glycol according to immersion temperature and time (Example 1).

In order to investigate the swellability of in situ hydrogels of the invention, the hydrogel discs having the weight of 2 g prepared in Example 1 above were immersed in PBS (pH 7.4) and then, stored in a refrigerator of 4 r and a water bath of 37 t, respectively for 1 to 7 days. The swellability was calculated by calculation formula 1 below and the results according to immersion temperature and time are shown in FIG. 2.

$$\text{Swellability} = W_t/W_0 \quad \text{[Calculation Formula 1]}$$

($W_t$: weight of hydrogels after immersion of t hours, $W_0$: weight of initial hydrogels)

At 4° C., it showed a constant swellability, but in the case of immersion at 37° C., it showed a constantly increasing tendency. It may be explained by the degradation of crosslinked polymers by hydrolysis.

EXPERIMENTAL EXAMPLE 8

In Vitro Degradation Test

Figure 3:
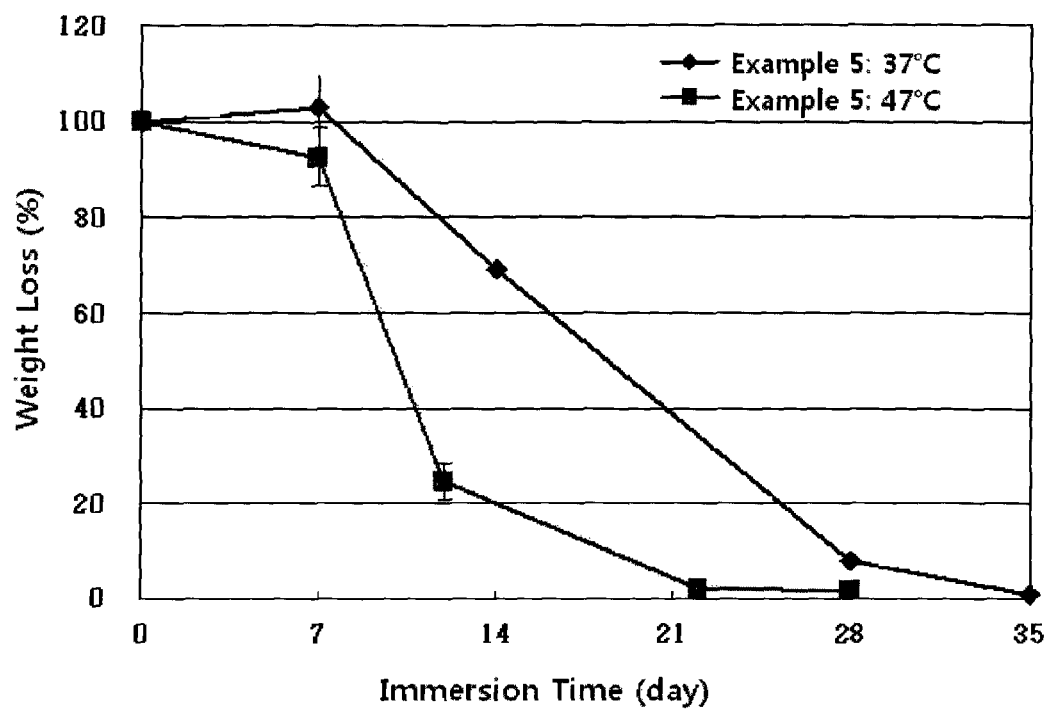
FIG. 3 is a graph showing the degradation of the hydrogel prepared by the crosslinking reaction of the activated γ-polyglutamic acid derivative and the polyethylene glycol.

In order to see degradation behavior of hydrogel, 1 g of the hydrogel prepared according to Example 5 was put into a 50 ml PBS and immersed in an insulated bath of 37° C. and 47° C., and of 50 rpm for a certain period of time (1 to 5 weeks, one week interval), and its observation results are shown in FIG. 3. Weight changes by the hydrolysis of the hydrogel were measured in terms of weight ratio before and after degradation through lyophilization.

As seen in FIG. 3 which shows weight loss results by the hydrolysis of the hydrogel, when the temperature of PBS was 47° C., the hydrogel started to be rapidly degraded after the lapse of one week and was all degraded within three weeks, and when the temperature of PBS was 37° C., it started to be slowly degraded after the lapse of one week, 10% or so of its initial weight was left at 4 weeks, and it was completely degraded at 5 weeks. Accordingly, since the hydrogel according to a preferred embodiment of the invention starts to be degraded after initial one week when wound healing is complete, and is completely degradable within two months, it can be concluded to have a desirable degradation behavior.

What is claimed is:

1. A γ-polyglutamic acid derivative of chemical formula 1:

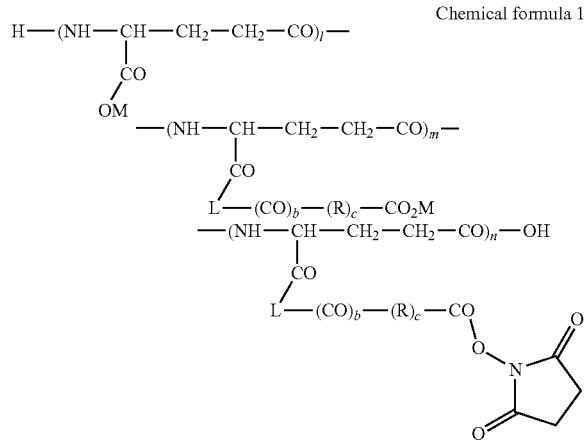

Chemical formula 1 wherein, a total sum of l, m, and n is an integer of 390 to 15,500, a ratio of l, m, and n is l:m:n=0 to 0.5:0.2 to 0.5:0.2 to 0.8, L is a linker, M is each independently H, an alkali metal or alkali earth metal, R is $CH_2$, b is 0 or 1, and c is an integer of 1 to 5.

2. The γ-polyglutamic acid derivative of claim 1, wherein the linker is —HN—(R)a-O—, wherein R is $CH_2$ and a is an integer of 1 to 5.

3. The γ-polyglutamic acid derivative of claim 2, wherein the linker is derived from aminomethanol, 1-amino-2-propanol, 1-amino-3-propanol, 1-amino-4-butanol, 1-amino-5-pentanol, or 2-aminoethanol.

4. The γ-polyglutamic acid derivative of claim 1, wherein —(CO)b-(R)c-CO— is —$CH_2CH_2CH_2CH_2$—CO—, —CO—$CH_2CH_2CH_2$—CO—, —$CH_2CH_2$—CO—, —CO—$CH_2CH_2$—CO—, or —$CH_2$—CO—.

5. A method of preparing the γ-polyglutamic acid derivative of claim 1, which comprises a first step of reacting a γ-polyglutamic acid with a lower alkanolamine having 1to 5 carbon atoms to form a γ-polyglutamic acid-alkanolamine;

a second step of reacting the γ-polyglutamic acid-alkanolamine with an anhydride of an acid selected from the group consisting of glutaric acid and succinic acid, or 1-halo alkanoic acid selected from the group consisting of 1-halo valeric acid, 1-halo propionic acid and 1-halo methylcarbonic acid to form a carboxyl terminal to which an alkyl group is attached; and a third step of reacting the thus formed carboxyl terminal with N-hydroxysuccinimide or N-hydroxysulfosuccinimide to form the γ-polyglutamic acid derivative.

6. The method of preparing the γ-polyglutamic acid derivative according to claim 5, wherein in the first step, the lower alkanolamine is reacted in a molar ratio of 0.1 to 2 with regard to a mole unit of the carboxyl groups of the γ-polyglutamic acid.

7. The method of preparing the γ-polyglutamic acid derivative according to claim 5, wherein in the second step, the anhydride of an acid or 1-halo alkanoic acid is reacted in a molar ratio of 3 to 8 with regard to a mole unit of the lower alkanolamine which forms the γ-polyglutamic acid-alkanolamine.

8. The method of preparing the y-polyglutamic acid derivative according to claim 5, wherein in the third step, the N-hydroxysuccinimide or N-hydroxysulfosuccinimide is reacted in a molar ratio of 0.1 to 3 with regard to a mole unit of the formed carboxyl terminal.

9. A hydrogel comprising a crosslinked body obtained by crosslinking the γ-polyglutamic acid derivative of claim 1, and a polyethylene glycol based polymer having a plurality of nucleophilic functional groups.

10. The hydrogel of claim 9, wherein the nucleophilic functional groups are an amine group, thiol group, or hydroxyl group.

11. The hydrogel of claim 9, wherein the polyethylene glycol based polymer is represented by chemical formula 2:

Chemical formula 2 wherein, I is a radical derived from 2 to 12 polyhydric alcohol, X represents an amine group, thiol group or hydroxyl group, n is 19 to 170, and m is an integer of 2 to 12, which is equal to the number of the hydroxyl groups of the polyhydric alcohol which I is derived from.

12. The hydrogel of claim 11, wherein the polyethylene glycol based polymer is represented by chemical formula 3 or 4:

Chemical formula 3

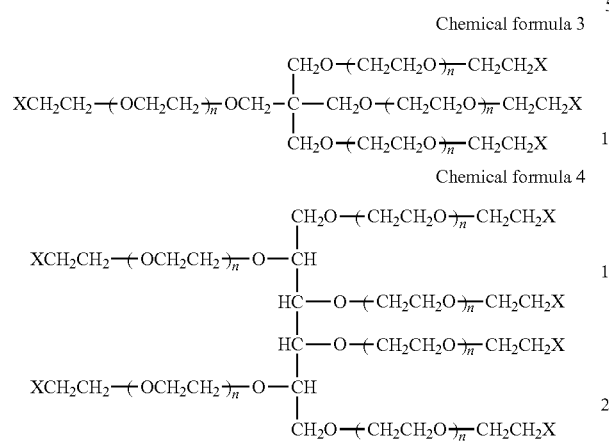

Chemical formula 4 wherein X represents an amine group, thiol group or hydroxyl group, and n is 19 to 170.

13. The method of claim 5, wherein the linker is —HN—(R)a-O—, wherein R is $CH_2$ and a is an integer of 1 to 5.

14. The method of claim 13, wherein the linker is derived from aminomethanol, 1-amino-2-propanol, 1-amino-3-propanol, 1-amino-4-butanol, 1-amino-5-pentanol, or 2-aminoethanol.

15. The method of claim 5, wherein —(CO)b-(R)c-CO— is —$CH_2CH_2CH_2CH_2$—CO—, —CO—$CH_2CH_2CH_2$—CO—, —$CH_2CH_2$—CO—, —CO—$CH_2CH_2$—CO—, or —$CH_2$—CO—.

16. The hydrogel of claim 9, wherein the linker is —HN—(R)a-O—, wherein R is $CH_2$ and a is an integer of 1 to 5.

17. The hydrogel of claim 16, wherein the linker is derived from aminomethanol, 1-amino-2-propanol, 1-amino-3-propanol, 1-amino-4-butanol, 1-amino-5-pentanol, or 2-aminoethanol.

18. The hydrogel of claim 9, wherein —(CO)b-(R)c-CO— is —$CH_2CH_2CH_2CH_2$—CO—, —CO—$CH_2CH_2CH_2$—CO—, —$CH_2CH_2$—CO—, —CO—$CH_2CH_2$—CO—, or —$CH_2$—CO—.

19. A γ-polyglutamic acid derivative comprising a repeating unit of chemical formula 5, a repeating unit of chemical formula 6 and a repeating unit of chemical formula 7:

—(A)$_l$—      Chemical formula 5

—(B)$_m$—      Chemical formula 6

—(C)$_n$—      Chemical formula 7 wherein,

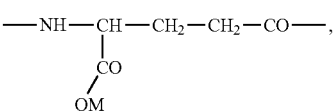

A is
B is

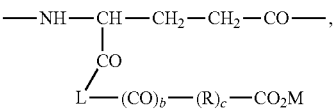

and
C is

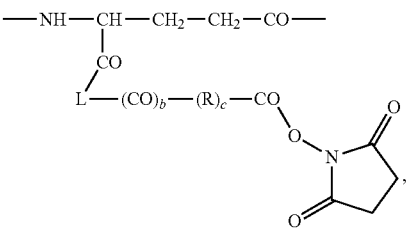

where a total sum of l, m, and n is an integer of 390 to 15,500,
a ratio of l to m to n is 0 to 0.5:0.2 to 0.5:0.2 to 0.8,
L is a linker, M is each independently H, an alkali metal or alkali earth metal, R is $CH_2$,
b is 0 or 1, and
c is an integer of 1 to 5.

* * * * *